(12) United States Patent
Liebschner (10) Patent No.: US 7,361,369 B2
(45) Date of Patent: Apr. 22, 2008

(54) IMPLANT WITH STRUCTURE ALLOWING INJECTION OF POLYMER FOR ATTACHING IMPLANT TO TISSUE

(75) Inventor: Michael A. K. Liebschner, Pearland, TX (US)

(73) Assignee: William Marsh Rice University, Houston, TX (US)

( * ) Notice: Subject to any disclaimer, the term of this patent is extended or adjusted under 35 U.S.C. 154(b) by 298 days.

(21) Appl. No.: 10/505,574

(22) PCT Filed: Feb. 28, 2003

(86) PCT No.: PCT/US03/06076

§ 371 (c)(1),
(2), (4) Date: Feb. 18, 2005

(87) PCT Pub. No.: WO03/073912

PCT Pub. Date: Sep. 12, 2003

(65) Prior Publication Data

US 2005/0129726 A1    Jun. 16, 2005

Related U.S. Application Data

(60) Provisional application No. 60/360,460, filed on Feb. 28, 2002.

(51) Int. Cl.
| | |
|---|---|
| *A61F 2/00* | (2006.01) |
| *C12N 11/14* | (2006.01) |
| *C12N 11/02* | (2006.01) |
| *C12N 11/08* | (2006.01) |
| *C07K 17/02* | (2006.01) |
| *C07K 17/08* | (2006.01) |
| *C07K 17/14* | (2006.01) |

(52) U.S. Cl. ............... 424/426; 424/423; 435/176; 435/177; 435/180; 530/811; 530/812; 530/815

(58) Field of Classification Search ........... None
See application file for complete search history.

(56) References Cited

U.S. PATENT DOCUMENTS

| 4,682,951 A | 7/1987 | Linkow |
| 5,702,446 A | 12/1997 | Schenck |
| 5,922,025 A | 7/1999 | Hubbard ............... 623/11 |
| 5,990,194 A | 11/1999 | Dunn et al. ............ 523/113 |
| 6,132,468 A | 10/2000 | Mansmann ........... 623/20.16 |
| 6,309,635 B1 | 10/2001 | Ingber et al. ........... 424/93.7 |
| 6,409,764 B1 | 6/2002 | White et al. |
| 2001/0021852 A1 | 9/2001 | Chappius |

FOREIGN PATENT DOCUMENTS

| CA | 1078551 | 6/1980 |
| WO | WO01/28461 | 4/2001 |
| WO | WO01/43625 | 6/2001 |
| WO | WO01/45585 | 6/2001 |

OTHER PUBLICATIONS

EPO Search Report for International Application EP03711293.5; dated Dec. 21, 2005.
Foreign communication from a related counterpart application—European Patent Office Examination Report, Application No. 03 711 293.5-2310, Jul. 26, 2007, 3 pgs.

*Primary Examiner*—David M. Naff
(74) *Attorney, Agent, or Firm*—Conley Rose, P.C.; Rodney B. Carroll; Albert K. Shung (57) ABSTRACT

Methods and apparatus for bone implants that allow for the directed application of an osteogenic compound. The implant is preferably constructed of a biodegradable polymer formed into a structure having micro-architectural features and includes features that allow for in-situ application of a liquid biodegradable polymer to securely attach the implant to the surrounding tissue. The implant is constructed with a nozzle connected to a fluid supply that can be injected through a central channel and one or more distribution channels. The implant is designed so as to provide structural support to the damaged area. The implant and the fluid supply are preferably biodegradable polymers that contain an osteogenic material.

20 Claims, 5 Drawing Sheets

IMPLANT WITH STRUCTURE ALLOWING INJECTION OF POLYMER FOR ATTACHING IMPLANT TO TISSUE

This application is a 371 of PCT/US03/06076, filed Feb. 28, 2003, which claims benefit of provisional application 60/360,460, filed Feb. 28, 2002.

STATEMENT REGARDING FEDERALLY SPONSORED RESEARCH OR DEVELOPMENT

Not applicable.

FIELD OF THE INVENTION

The present invention generally relates to the field of medical devices or implants. More specifically, the present invention relates to implantable structures that have integrated features that allow for controlled fusion of the implanted structure to the native tissue.

BACKGROUND OF THE INVENTION

Tissue engineering extends into a diverse range of disciplines that includes chemistry, biology, and engineering. The applications of these principles toward the human body can directly affect the quality of life for people suffering from afflictions as common as osteoarthritis to those as serious as heart disease. The many potential benefits of tissue engineering include the development or revolution of current technology in total hip, knee, cartilage, tendon, and vascular tissue replacement. Many of these practices at present involve implanting either an autologous, allologous, or synthetic graft in place of the damaged area. Within the body, the implant must satisfy requirements pertaining to biocompatibility as well as functional and mechanical stability. Unfortunately, many materials react compatibly with the body but cannot meet the long-term mechanical, geometrical, and functional requirements of the body.

In contrast with many conventional procedures and materials, tissue engineering aims to repair, restore, or regenerate living tissue instead of replacing it with a synthetic implant. One approach to tissue engineering is to provide the body with a basic scaffold that mimics the natural structure of the tissue while providing a temporary functional support. When the appropriate cells are attached to the scaffold, they will proliferate and differentiate into the desired phenotype. If the cells can be culled from the body and propagated in vitro into a viable implant, then the device can be installed in the system and possibly operate as smoothly as healthy tissue. Ideally, the scaffold would then slowly degrade within the body, allowing the body to replace the artificial matrix with a natural one.

Of the types of tissues in the body, the connective tissues seem to offer a great deal of promise for using scaffolds. Examples of connective tissues include ligaments, tendons, cartilage, bone, etc. Without wishing to be bound by a particular theory, it is believed that this is due to the morphology of the connective tissues; the connective tissues comprise cells in various matrices (i.e. semi-solid, solid elastic, and solid rigid). The matrix structure of the connective tissues allows for a scaffold implant to be easily received and incorporated into the tissue.

The first step towards tissue engineering is to characterize the tissue's mechanical, biochemical, structural, and functional properties. Then a search begins for the material or combinations of materials that will meet all the characteristics determined initially. The struggle to find the perfect material often results in weighing the criteria against each other and choosing the most important factors in the success of the implant. For example, in bone repair or replacement the most important function that the implant must perform is to bear the load placed on it by the body over time. The other functions of the bone, such as housing the bone marrow that produces red blood cells, are less important, as long as the rest of the body can make up the red blood cell production. Therefore the preferred materials for bone replacement have traditionally been metals, e.g. titanium, and ceramics, e.g. calcium phosphate ceramics, with high compressive strengths. These traditional materials lack certain desired properties and are therefore not entirely satisfactory.

Because the field of tissue engineering is constantly changing, based on the improved understanding of the body, there remains a need in the art for methods and apparatus to improve tissue stabilization and/or regeneration.

SUMMARY OF THE INVENTION

Accordingly, there are provided herein methods and apparatus for implants that provide structural support to the surrounding tissue and act as a scaffold to support and promote the growth of new tissue. The implants are preferably constructed of a biodegradable polymer formed into a structure having micro-architectural features that allow for in-situ application of a liquid biodegradable polymer to securely attach the implant to the surrounding tissue.

One embodiment of a preferred implant is preferably an implant having two portions, namely an outer portion that is substantially impermeable to fluid and an inner portion. In conjunction with the outer portion is a nozzle, extending through the outer portion and adapted for connection to a fluid supply, and a central channel, in fluid communication with the nozzle and extending through the inner portion. Connected to the central channel are one or more distribution channels extending laterally from the central channel to the outside of the implant. The implant preferably comprises a plurality of structural members that interconnect the channels and the outer portion to form a unitary structure.

The present implant is preferably constructed as a single piece from a biodegradable polymer, such as poly(propylene fumarate) (PPF) or some other polymer whose strength and toughness are suitable for use in the native tissue. The polymer implant is preferably constructed by stereolithography, three-dimensional printing, or some other technique that allows for the construction of precise, micro-architectural structures. The polymer may be cross-linked by any suitable treatment, including but not limited to radiation or chemical reaction. It is also preferred that the implant also include tissue growth promoters such as TGF-$\beta$, estrogen or bone morphogenetic proteins (BMPs).

The nozzle is preferably adapted to receive a syringe or apparatus that can be used to supply a fluid that is preferably a liquid mixture of a biodegradable polymer and a tissue growth promoter. In bone applications, one preferred mixture includes PPF and one or more BMP. Once the implant is placed into a pre-prepared cavity in the bone, the liquid mixture is injected into the implant. The lateral channels direct the flow toward the bottom and sides of the implant. The liquid mixture is preferably injected at a sufficient pressure to locally displace bone marrow without yielding the surrounding bone material. This allows the liquid mixture to flow between the bone tissue's micro-architectural structures in a quasi-controlled fashion. The liquid polymer mixture is then allowed to cure, thereby securely attaching the implant to the bone.

Once the implant is anchored in the bone, the nozzle can be removed from the implant, thus providing a smooth outside surface of the implant. As the liquid polymer is injected into the implant, bodily fluids fill the interstitial areas within the body of the implant. The osteogenic materials in both the implant structure and/or the injected materials promote the growth of bone cells in the implanted area. The structure of the implant also provides support to the surrounding tissue and acts as a scaffold on which new bone cells can grow.

Thus, the present invention comprises a combination of features and advantages that enable it to substantially improve the application of bioengineered polymers and tissue growth promoters. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

For a more detailed understanding of the preferred embodiments, reference is made to the accompanying Figures, wherein.

DETAILED DESCRIPTION OF THE PREFERRED EMBODIMENTS

In the description that follows, like parts are marked throughout the specification and drawings with the same reference numerals, respectively. The drawing figures are not necessarily to scale. Certain features of the invention may be shown exaggerated in scale or in somewhat schematic form and some details of certain elements may be omitted in the interest of clarity and conciseness.

The present invention relates to methods and apparatus for delivering a stable structure and possibly stimulating tissue regeneration in a damaged area. The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein. In particular, various embodiments of the present invention provide a number of different constructions of implants that support the delivery of a bioactive material. Reference is made to a cylindrical implant having tubular components as one example of such an implant, but the use of the present invention is not limited to the cylindrical and tubular shapes and may be constructed in any shape suited to the particular damaged area needing repair. In addition, the micro-architectural design or open cell architecture may be constructed in a variety of forms, including but not limited to, honeycomb, tetragonal, and circular. It is to be fully recognized that the different teachings of the embodiments discussed below may be employed separately or in any suitable combination to produce desired results.

As discussed above, in bone repair or replacement the most important function that the implant must perform is to bear the loads placed on it by the body over time. Bone is generally comprised of on outer layer of cortical bone tissue, which is a hard, solid bone tissue, and an inner core of trabecular bone tissue, which is very porous. Cortical bone tissue is substantially solid bone with a typical porosity of 10%. In contrast, trabecular bone is a network of small, interconnected plates and rods of individual trabeculae with relatively large spaces between the trabeculae. Trabecular bone has a porosity of 50-90%.

As a general rule, bone is stronger in compression than in tension and cortical bone is stronger than trabecular bone. Ranges of reported elastic modulus have been from 10 MPa to 25 GPa (10 MPa to 2 GPa for cancellous bone; 4 to 25 GPa for cortical and cancellous bone); compressive strength between 40 and 280 MPa (40 to 280 MPa for cancellous bone; 138 to 193 MPa for cortical bone); and tensile strength between 3.5 MPa and 150 MPa (3.5 to 150 MPa for cancellous bone; 69 to 133 MPa for cortical bone).

Mechanisms by which bone may fail include brittle fracture from impact loading and fatigue from constant or cyclic stress that may act in tension, compression, and/or shear along one or more of the axes of the bone. Therefore, synthetic bone substitutes should have a comparable elastic modulus to that of bone to ensure that the implant will be structurally sound when subject to physiological and hyperphysiological stresses. In addition, implants having a comparable elastic modulus to the native tissue help prevent bone resorption, which is the degradation of tissue surrounding the implant caused by decreased local mechanical loading of the bone tissue surrounding the implant.

Figure 1:
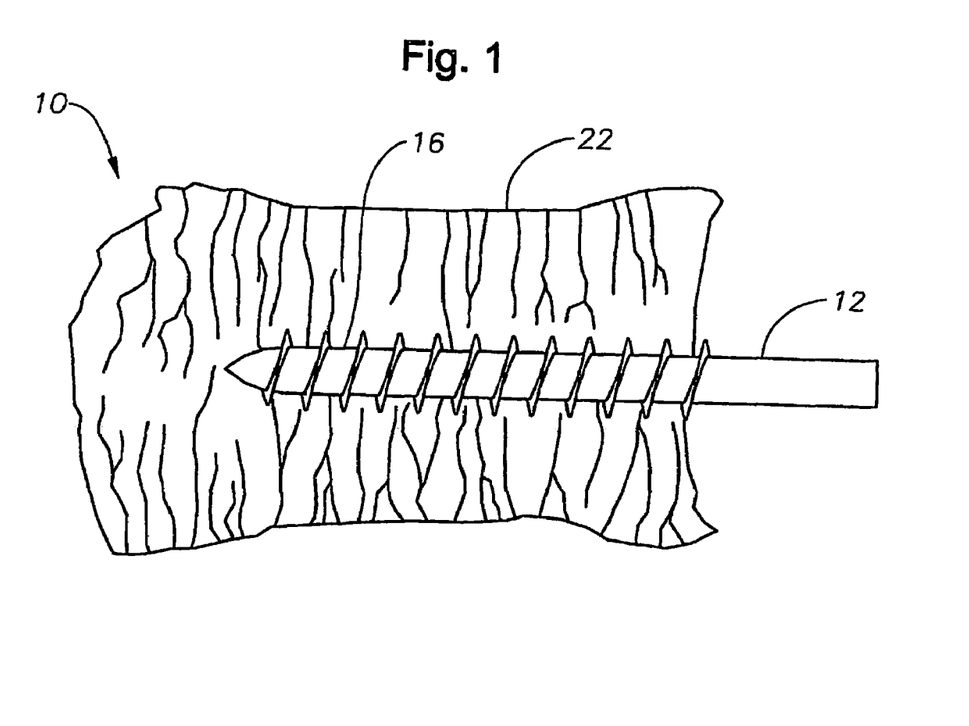
FIG. 1 is a CT scan of a prior art bone screw.

Referring initially to FIG. 1, a computer tomography image (CT scan) of a prior art system 10 comprising a metal screw 12 in a section of bone 22 is shown. The metal screw 12 is conventionally fabricated from titanium or stainless steel and can be coated 16 with hydroxyapatite. As can be appreciated, the relative surface area of screw 12 in close contact with bone tissue 22 is minimal. This is because the surface area of the screw 12 is somewhat limited and because screw 12 is substantially nonporous, preventing bone tissue 22 from penetrating screw 12. As a result, the force necessary to remove screw 12 from bone tissue 22 in the well-known "pull-out test" is small, indicating that the chance of failure is great.

Figure 2:
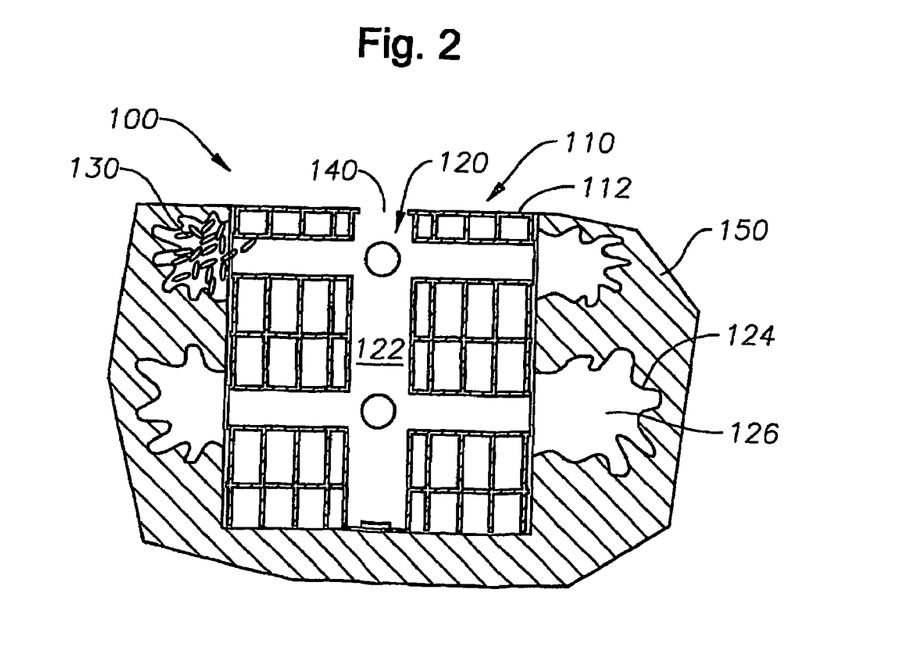
FIG. 2 is a section view of an implant made in accordance with the principles of present invention and implanted in tissue.

Referring now to FIG. 2, the present invention generally includes three elements: an open cell architecture 110 defining a scaffold 112, a system of interconnected conduits 120 extending throughout the scaffold 112, and an injection port or opening 140. A scaffold device or implant 100 made according to the present invention incurs a number of structural and functional benefits. For example, the open cell architecture 110 provides structural support equivalent to that of the native tissue and allows surrounding cells and tissues 150 to migrate into the implant 100, such that vascularization is achieved (not shown).

The system of interconnected conduits 120 allows a gel or cement 122 to flow through the implant 100 and into regions of tissue 150 surrounding the implant, fixating the implant 100 in the body. The gel or cement 122 often forms irregularly shaped pools 124, such as finger-like protrusions 126. Finger-like protrusions 126 are desirable because they can increase the tissue interaction with a larger surrounding volume while keeping its own volume small and because they increase the amount of force necessary to remove implant 100 from surrounding tissue 150 in the pull-out test. In this manner, implant 100 is securely mounted in surrounding tissue 150.

The injection port or opening 140 allows the gel or cement 122 to be easily set in the implant 100. In addition, injection port 140 may be configured in a number of ways including adapted to receive a syringe or threaded to engage an outer portion, such as a tissue covering, e.g. a bone plate, (not shown).

The open cell architecture 110 of scaffold 112 is preferably fabricated from a polymeric material chosen from the group consisting of poly(paradioxanone) (PDS), poly(dl-lactic acid) (PLA), poly(dl-glycolic acid) (PGA), poly(propylene fumarate) (PPF), and copolymers of dl-lactic acid and dl-glycolic acid (PLG). Additionally, biodegradable polymers currently used in in vivo applications which are well suited to implantation, as described by Kulkarni, et al., J. Biomedical Materials Research, 5, 169-81 (1971); Hollinger, J. O. and G. C. Battistone, "Biodegradable Bone Repair Materials," Clinical Orthopedics and Related Research, 207, 290-305 (1986), incorporated herein by reference, may also be used.

The gel or cement 122 is preferably fabricated from a polymer-based material chosen from the group consisting of poly(methyl methacrylate) (PMMA), PDS, PLA, PGA, PPF, and PLG. Additionally, gel or cement 122 may comprise any suitable composition for use in the body, including calcium and phospate-containing ceramic cements. In some embodiments, the addition of inclusions 130 may be used in cement 122 in order to create pores or voids (not shown) in the hardened structure in conduits 120 and in finger-like protrusions 126. The inclusions may be micro or nano-sized particles of any geometry. The presence of voids may allow for additional vascularization (not shown) within implant 100.

Additionally, tissue growth promoters or bioactive materials may be incorporated into implant 100 in the cement 122 and/or in the scaffold 112. Tissue growth promoters are preferably chosen from the group consisting of members of the transforming growth factor beta superfamily, bone morphogenic proteins, basic fibroblast growth factor, platelet derived growth factor, insulin like growth factor, and extracellular matrix molecules including osteopontin, osteonectin, osteocalcin, and bone sialoprotein. Suitable protein fragments include fragments of the members of the same compounds, comprising 3-30 amino acids. Preferably, the presence of tissue growth promoters encourages the growth of new tissue on the implant structure.

In some embodiments it may be desirable for the scaffold 112 and/or the cement 122 to be biodegradable. Biodegradable implants are generally desirable in younger patients, who are capable of regenerating new tissue. With a biodegradable implant, as tissue begins to grow in the implanted area, implant 100 will gradually be absorbed into the body. Preferably the degradation properties are such that the tissue will fill in the damaged area by the time implant 100 is completely absorbed. Scaffold 112 and cement 122 may have similar or disparate degradation properties. By varying the composition and cross-linking of the polymers, the degradation time and other properties of the polymers can be adjusted.

In other embodiments, it may be desirable for either the scaffold 112 and/or cement 122 to be permanent or nonbiodegradable. Permanent implants are generally used in older patients, who are not capable of regenerating sufficient new tissue. When permanent implants are desirable, scaffold 112 is preferably fabricated from materials selected from the group consisting of biocompatible polymers, ceramics, and metals. Suitable metals include titanium and stainless steel.

Figure 3:
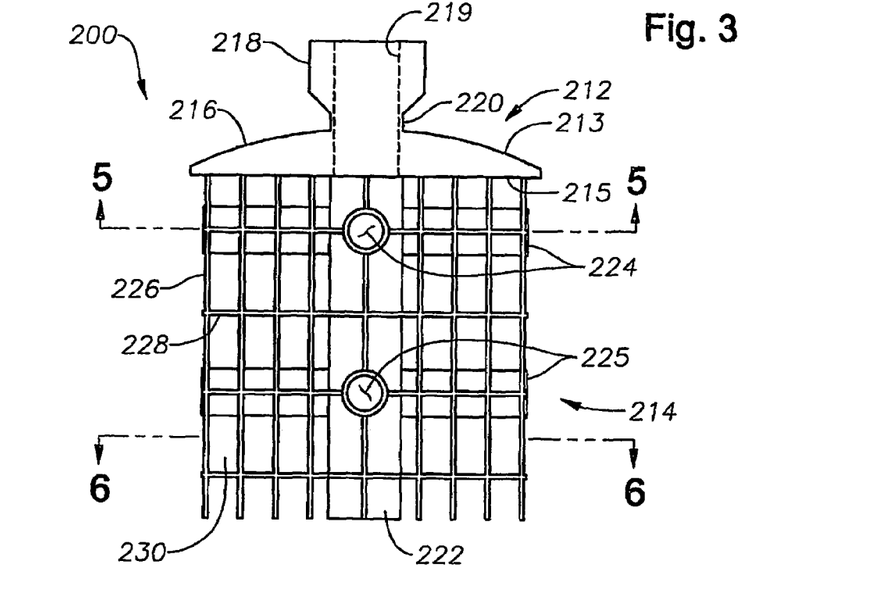
FIG. 3 is an elevation view of one embodiment of an implantable bone plug.

Referring now to FIGS. 3-8, an example of an implant 200 made in accordance with the present invention is shown in a number of views. In FIG. 3, one embodiment of the present implant 200 comprises an outer portion 212 and an inner portion 214. Outer portion 212 comprises a substantially solid cap 216 and a nozzle 218. Cap 216 preferably has convex outer surface 213 and a generally flat inner edge 215. Nozzle 218 extends from outer surface 213 and has a reduced diameter neck portion 220. Nozzle 218 includes a bore 219 therethrough. Inner portion 214 comprises a center channel 222 from which extend a plurality of radial channels comprising a set of upper channels 224 and lower channels 225. Center channel 222 and radial channels 224,225 are connected to upper portion 212 and in fluid communication with bore 219 through nozzle 218. Inner portion 214 also comprises a plurality of interconnected vertical and horizontal structural members 226,228 that interconnect to the walls of channels 222,224,225 and define a plurality of interstitial areas 230. The structural members 226,228 are also connected, or formed integrally with, solid cap 216 to form a unitized structure.

Figure 4:
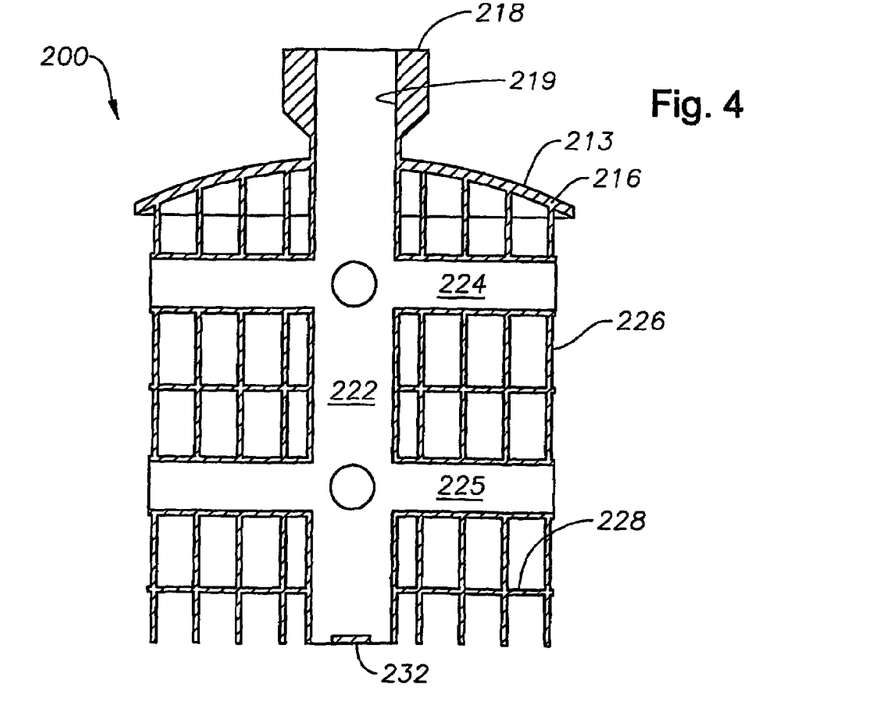
FIG. 4 is a section view of the bone plug of FIG. 1.

FIG. 4 represents a sectional view of implant 200 taken through the centerline and along a plane that intersects the center of upper horizontal channels 224. Center channel 222 extends from nozzle 218 to the base of implant 200, where a flow obstructer 232 is located across the opening of the channel. Flow obstructer 232 serves to restrict the flow of fluids out of the base of the channel and force the fluids to flow through the upper 224 and lower 225 channels. Flow obstructer 232 may comprise a plug or simply an opening that has a smaller diameter than channels 222,224,225.

Figure 5:
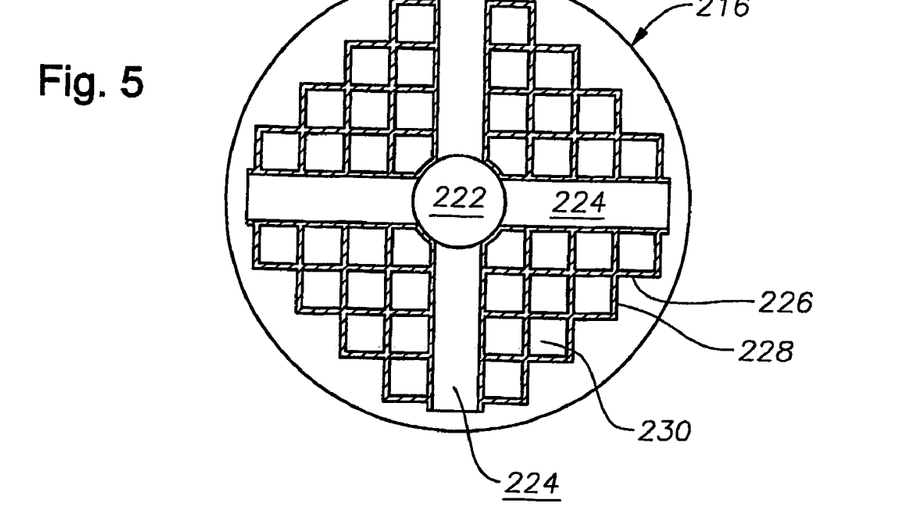
FIG. 5 is a section view of the bone plug of FIG. 1 taken along lines 5-5 of FIG. 3.
Figure 6:
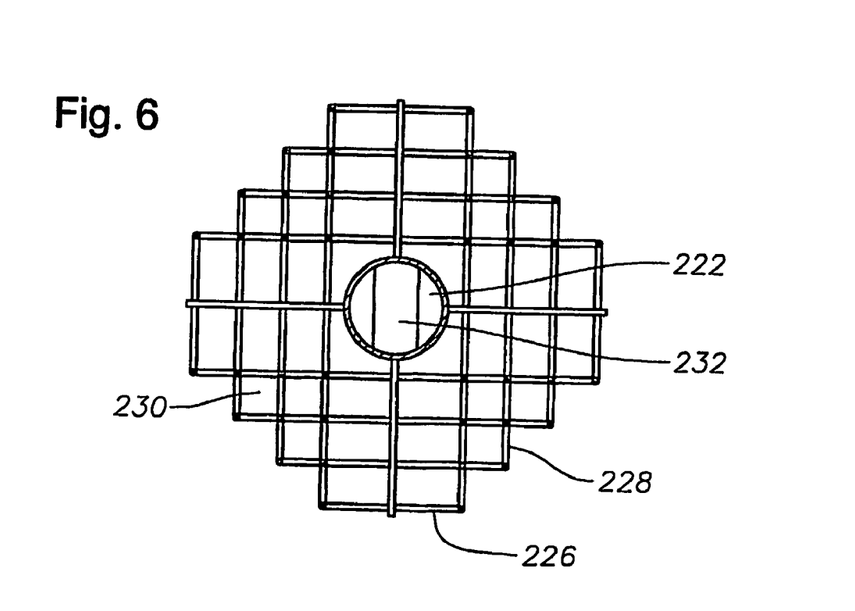
FIG. 6 is a section view of the bone plug of FIG. 1 taken along lines 6-6 of FIG. 3.

FIGS. 5 and 6 show cross-sections of implant 200 taken, respectively, along lines 5-5 and 6-6 in FIG. 3. FIG. 5 is a section taken through horizontal channels 224 looking toward the outer portion 212 of implant 200. In the embodiment shown, four upper horizontal channels 224 are equally spaced about and radially extend from center channel 222. Structural members 226,228 combine to form a rectangular lattice that connects the upper channels 224 to form a stable structure. FIG. 6 shows a section view taken at a plane below lower horizontal channels 225 looking toward the base of implant 200. Flow obstructer 232 blocks a portion of the outlet of center channel 222. Structural members 226, 228 create an interconnected structure supporting the center channel 222.

Implant 200 is preferably constructed from a biodegradable polymer, such as PPF, that has been combined with a material having osteogenic properties. The implant is preferably formulated to have strength and toughness properties close to the properties of the surrounding bone tissue. For example, the preferred material has an elastic modulus of between 200 MPa and 1 GPa, a compressive strength between 50 and 200 MPa, and a tensile strength of between 10 and 150 MPa. Materials such as demineralized bone matrix may be combined with the polymer to encourage the growth of bone cells on the structure. Implant 200 is preferably constructed as a single piece structure with the polymer being cured by chemical cross-linking, photo-cross linking, or other radiation cross-linking. Implant 200 may be constructed using three-dimensional printing, stereolithography, injection molding, or any other method used to build structures having micro-architectural features.

The embodiment shown in FIGS. 3-6 is constructed in a substantially cylindrical arrangement. Other embodiments may also be used, depending on the area needing repair. An implant of almost any desired size and shape can be constructed. The implants are preferably constructed so that the implant provides support to the surrounding bone tissue at least equal the support provided by natural bone tissue. Structural members 226,228 are preferably solid members having circular cross-sections and can be arranged in any manner necessary to provide the desired strength. Channels 222,224,225 are shown as extending through the total diameter of the implants, terminating at the implant/tissue interfaces. However, in some embodiments, channels 222,224, 225 may terminate inside the implants, such that channels 222,224,225 do not physically contact the surrounding tissue.

Figure 7:
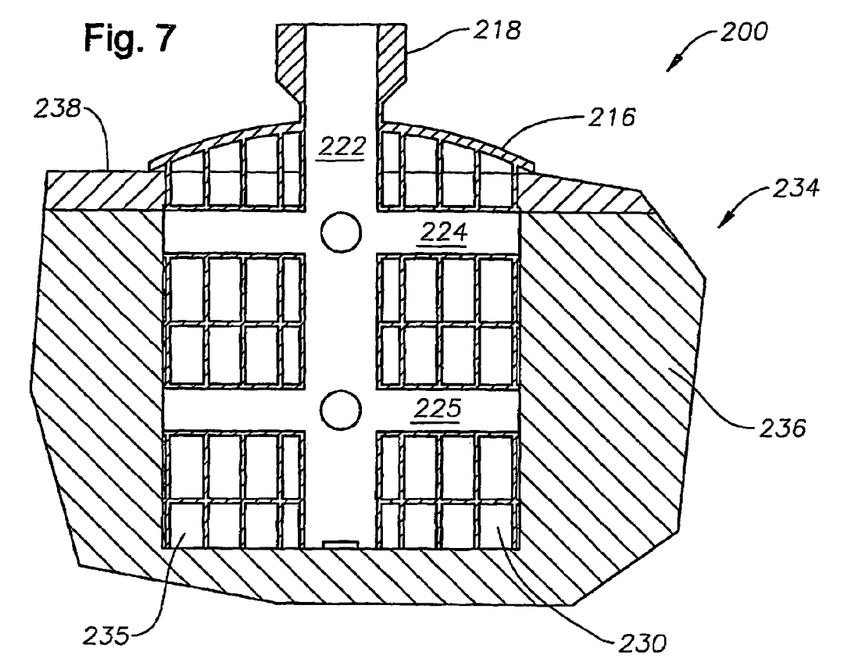
FIG. 7 is a section view of the bone plug of FIG. 1 implanted in a bone.

FIG. 7 shows implant 200 implanted into bone structure 234 having a cortical bone layer 238 and an underlying mass of trabecular bone tissue 236. In preparation for implant 200, a cavity 235 is made in bone 234 of a size that will accommodate the implant. Implant 200 is attached at nozzle 218 to a syringe (not shown) filled with a liquid osteogenic polymer. Once implant 210 is in place in bone cavity 235, the liquid polymer is injected through nozzle 218 and into center channel 222. The liquid polymer flows through horizontal channels 224,225 and into the surrounding trabecular bone tissue 236, while body fluids (blood, marrow, etc.) flow into the interstitial spaces 230 in the implant.

Figure 8:
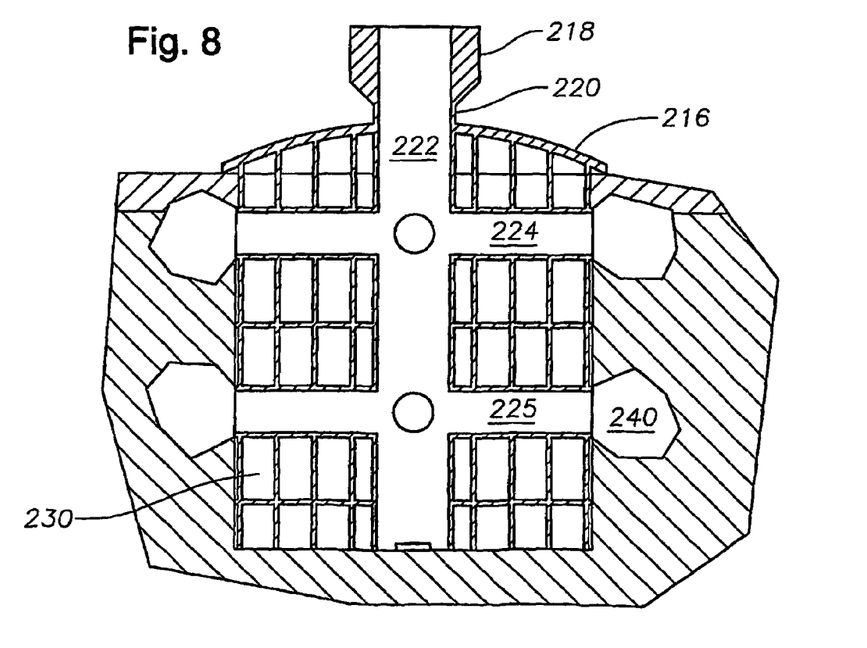
FIG. 8 is a section view of the bone plug of FIG. 7 after injection of a liquid.

Referring now to FIG. 8, the liquid polymer is preferably injected at a pressure sufficient to locally force the liquid polymer between the bone micro-architecture tissue 236 so as to form interlock cavities 240 between bone tissue 236 and implant 200 adjacent to the outlet of each channel 224,225. Liquid polymer fills cavities 240 as solid cap 216 prevents excess body fluids from flowing out of the implant area. The liquid polymer then polymerizes and locks implant 200 to bone 234. Once the injected polymer has set and implant 200 is secured in position, nozzle 218 can easily be broken by applying a twisting and/or bending force to reduced diameter neck 220. The implanted area can then be allowed to heal naturally.

While FIGS. 3-8 have shown an implant made in accordance with the present invention for use in bone, it is contemplated that the present invention may be used in other connective tissues such as tendon and ligament repair and additionally for filling voids in hard connective tissue at other anatomical sites such as the hip, cranium, and jaw (e.g. tooth socket filling).

Figure 9:
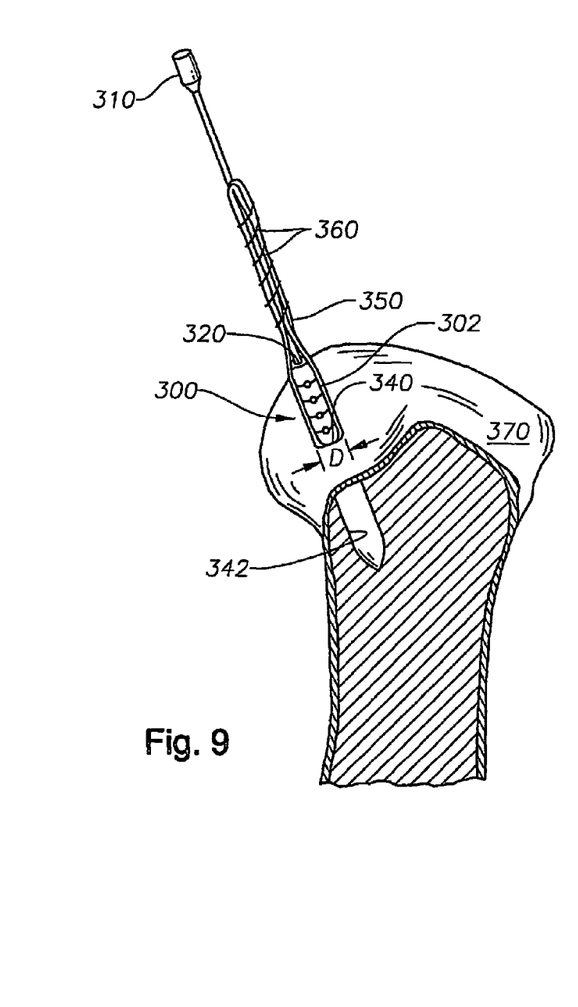
FIG. 9 is a section view of one embodiment of a ligament plug.

Referring now to FIG. 9, an example of implant or plug 300 used in ligament repair is shown. In some embodiments, a metal canula 310, used to deliver cement (not shown) to the plug 300, is attached to the injection port 320 of the plug 300. A tendon graft 350 is harvested from the patellar ligament (not shown), folded, and secured to the plug 300 using resorbable sutures 360. In some embodiments, a side 302 of the plug 300 has grooves (not shown) for receiving the tendon graft 350, which allows the graft 350 to pass along the plug side 302 without increasing the plug diameter D. The outer diameter of the ligament plug system is preferably approximately 8 mm. After drilling a socket hole 340 into the bone 370 with approximately the same diameter as the ligament plug system, the graft 350 is pushed into socket 342. A mallet or other suitable tool (not shown) is tapped onto the canula 310 until the plug 300 is fully seated inside the socket 342. The cement is injected through the injection port 320 and allowed to cure. The canula 310 is subsequently removed. Potential benefits associated with using an implant made in accordance with the present invention in ligament repair include (i) reduction of steps required to anchor a ligament graft to bone tissue and (ii) use of biodegradable materials which promote native tissue regeneration.

Figure 10:
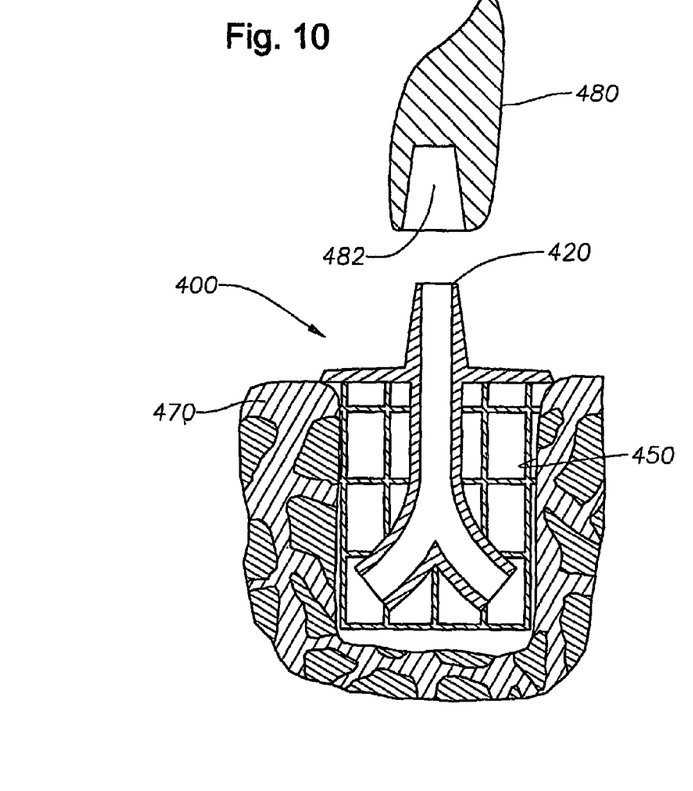
FIG. 10 is a section view of one embodiment of an implantable tooth socket plug.

Referring now to FIG. 10, an example of implant or plug 400 used to fill an extracted tooth socket 450 is shown. The plug 400 itself is preferably fabricated of titanium and follows the same micro-architecture described previously, however, on a much smaller scale. After tooth extraction, the socket 450 is prepared for implantation, as is known in the art. The plug 400 is then inserted into the socket 450 and cement (not shown) is injected through the injection port 420 using necessary injection tools (not shown). The cement is allowed to cure, thereby anchoring the plug 400 to the surrounding trabecular bone tissue 470. After removing the injection tools, an artificial tooth 480 can be seated onto the injection port 420 of the plug 400 via recess 482. Potential benefits associated with using an implant made in accordance with the present invention in tooth socket repair include (i) reduction of time required for a tooth socket to heal, (ii) secure anchorage of the implant to the surrounding bone tissue, and (iii) structural support for an artificial tooth.

The embodiments set forth herein are merely illustrative and do not limit the scope of the invention or the details therein. It will be appreciated that many other modifications and improvements to the disclosure herein may be made without departing from the scope of the invention or the inventive concepts herein disclosed. For example, while the example of a bone plug has been shown for use in a large bone, such as a femur, it should be understood that the present invention may also be used in other bones, including dental bones and teeth. Because many varying and different embodiments may be made within the scope of the inventive concept herein taught, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An implant comprising:
   a scaffold having an open cell structure defining a plurality of interstitial areas;
   a system of interconnected conduits extending throughout the scaffold; and
   at least one injection port in fluid communication with at least one of the conduits, whereby curable liquid polymer introduced into the implant via the injection port flows through the system of conduits.

2. The implant according to claim 1 wherein the curable liquid polymer incorporates one or more bioactive materials.

3. The implant according to claim 2 wherein the one or more bioactive materials is a tissue growth promoter selected from the group consisting of members of the transforming growth factor beta superfamily, bone morphogenic proteins, basic fibroblast growth factor, platelet derived growth factor, insulin like growth factor, and extracellular matrix molecules.

4. The implant according to claim 1 wherein the scaffold comprises a material chosen from the group consisting of biocompatible polymers, ceramics, and metals.

5. The implant according to claim 1 wherein the scaffold comprises a polymeric-based material chosen from the group consisting of poly(paradioxanone), poly(dl-lactic acid), poly(dl-glycolic acid), poly(propylene fumarate), and copolymers of dl-lactic acid and dl-glycolic acid.

6. The implant according to claim 5 comprising an amount of the curable liquid polymer in at least one of the conduits, wherein the curable liquid polymer comprises a material selected from the group consisting of poly(methyl methacrylate), poly(paradioxanone), poly(dl-lactic acid), poly(dl-glycolic acid), poly(propylene fumarate), and copolymers of dl-lactic acid and dl-glycolic acid.

7. The implant according to claim 6 wherein the scaffold, the curable liquid polymer, or both are biodegradable.

8. The implant according to claim 3 wherein the extracellular matrix molecules are selected from the group consisting of osteopontin, osteonectin, osteocalcin, bone sialoprotein, fragments thereof, and combinations thereof.

9. The implant according to claim 1 wherein the at least one injection port is a nozzle which is removable from the implant.

10. The implant according to claim 2 wherein the one or more bioactive materials comprises osteogenic material.

11. A method for stabilizing tissue comprising:
preparing a cavity of a predetermined size in the tissue;
inserting an implant into the cavity, the implant comprising:
a scaffold having an open cell structure defining a plurality of interstitial areas;
a system of interconnected conduits extending throughout the scaffold; and
at least one injection port in fluid communication with at least one of the conduits;
injecting a curable liquid polymer into the implant such that the curable liquid polymer flows through the system of conduits and into tissue surrounding the implant, thereby securing the implant in the tissue, and fluid from the tissue enters at least a fraction of the interstitial areas.

12. The method according to claim 11 wherein the curable liquid polymer incorporates one or more bioactive materials.

13. The method according to claim 12 wherein the one or more bioactive materials is a tissue growth promoter selected from the group consisting of members of the transforming growth factor beta superfamily, bone morphogenic proteins, basic fibroblast growth factor, platelet derived growth factor, insulin like growth factor, and extracellular matrix molecules.

14. The method according to claim 11 wherein the scaffold comprises a material chosen from the group consisting of biocompatible polymers, ceramics, and metals.

15. The method according to claim 14 wherein the scaffold comprises a polymeric-based material chosen from the group consisting of poly(paradioxanone), poly(dl-lactic acid), poly(dl-glycolic acid), poly(propylene fumarate), and copolymers of dl-lactic acid and dl-glycolic acid.

16. The method according to claim 15 wherein the curable liquid polymer comprises a material selected from the group consisting of poly(methyl methacrylate), poly(paradioxanone), poly(dl-lactic acid), poly(dl-glycolic acid), poly(propylene fumarate), and copolymers of dl-lactic acid and dl-glycolic acid.

17. The method according to claim 16 wherein the scaffold, the curable liquid material, or both are biodegradable.

18. The method according to claim 13 wherein the extracellular matrix molecules are selected from the group consisting of osteopontin, osteonectin, osteocalcin, bone sialoprotein, fragments thereof, and combinations thereof.

19. The method according to claim 11 wherein the at least one injection port is a nozzle which is removable from the implant.

20. The method according to claim 12 wherein the one or more bioactive materials comprises an osteogenic material.

* * * * *